(12) United States Patent
Schulz et al.

(10) Patent No.: US 11,420,867 B2
(45) Date of Patent: Aug. 23, 2022

(54) PROCESS FOR COMBINED PRODUCTION OF METHANOL AND AMMONIA

(71) Applicants: GASCONTEC AG, Basel (CH); THYSSENKRUPP INDUSTRIAL SOLUTIONS AG, Essen (DE)

(72) Inventors: Alexander Schulz, Frankfurt (DE); Johannes Völkl, Kelkheim (DE); Sina Kunz, Frankfurt (DE); Dierk Müller, Karben (DE); Ulrich Koss, Bad Homburg von der Höhe (DE)

(73) Assignees: GASCONTEC AG, Basel (CH); THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 16/754,868

(22) PCT Filed: Oct. 8, 2018

(86) PCT No.: PCT/EP2018/077320
§ 371 (c)(1),
(2) Date: Apr. 9, 2020

(87) PCT Pub. No.: WO2019/072762
PCT Pub. Date: Apr. 18, 2019

(65) Prior Publication Data
US 2021/0198105 A1 Jul. 1, 2021

(30) Foreign Application Priority Data
Oct. 9, 2017 (EP) ..................................... 17195544

(51) Int. Cl.
*C01B 3/02* (2006.01)
*C01B 3/12* (2006.01)
(Continued)

(52) U.S. Cl.
CPC ................ *C01B 3/025* (2013.01); *C01B 3/12* (2013.01); *C01B 3/50* (2013.01); *C07C 29/1518* (2013.01);
(Continued)

(58) Field of Classification Search
CPC ................ C07C 31/04; C07C 29/1518; C01B 2203/068; C01B 2203/061;
(Continued)

(56) References Cited

U.S. PATENT DOCUMENTS

| 4,469,665 A | * | 9/1984 | Pinto | ...................... B01D 53/04 423/359 |
| 5,173,513 A | * | 12/1992 | Pinto | .................... C07C 29/1512 518/702 |
| 2009/0019767 A1 | * | 1/2009 | Abughazaleh | ............ C01B 3/16 48/61 |

FOREIGN PATENT DOCUMENTS

| DE | 3712008 A1 | 10/1988 |
| DE | 102004013539 A1 | 10/2005 |

(Continued)

OTHER PUBLICATIONS

International Search Report dated Nov. 7, 2018 re: Application No. PCT/EP2018/077320, pp. 1-2, citing: WO2005095313 A1, DE 102007008690 A1 and DE 3712008 A1.

*Primary Examiner* — Jafar F Parsa
(74) *Attorney, Agent, or Firm* — Cantor Colburn LLP

(57) ABSTRACT

A process for the combined production of methanol and ammonia, wherein a reactant stream includes carbon monoxide is supplied to a recovery assembly to obtain first and second hydrogen-containing streams, each having an increased molar proportion of hydrogen compared to the reactant stream. The recovery assembly includes a shift conversion in which the carbon monoxide of at least one carbon monoxide-containing stream is at least partially (Continued)

converted into hydrogen and carbon dioxide by reaction with steam to obtain a converted stream having hydrogen and carbon dioxide at least partially recycled to a hydrogen recovery from which the first and second hydrogen-containing streams are obtained. A nitrogen stream and, at least partially, the first hydrogen-containing stream are supplied to an ammonia reactor assembly for at least partial conversion into ammonia and, at least partially, the second hydrogen-containing stream is supplied to a methanol reactor assembly for at least partial conversion into the methanol.

14 Claims, 6 Drawing Sheets

(51) Int. Cl.
*C01B 3/50* (2006.01)
*C07C 29/151* (2006.01)
*C07C 31/04* (2006.01)

(52) U.S. Cl.
CPC ...... *C01B 2203/0288* (2013.01); *C01B 2203/043* (2013.01); *C01B 2203/0475* (2013.01); *C01B 2203/061* (2013.01); *C01B 2203/068* (2013.01); *C07C 31/04* (2013.01)

(58) Field of Classification Search
CPC .... C01B 2203/0475; C01B 2203/0288; C01B 3/50; C01B 2203/0283
See application file for complete search history.

(56) References Cited

FOREIGN PATENT DOCUMENTS

| DE | 102007008690 A1 | 8/2008 |
|----|-----------------|--------|
| WO | 2005095313 A1 | 10/2005 |

\* cited by examiner

PROCESS FOR COMBINED PRODUCTION OF METHANOL AND AMMONIA

TECHNICAL FIELD

The disclosure relates to a process and a plant for combined production of methanol and ammonia, wherein a reactant stream with carbon monoxide is supplied to a recovery assembly to obtain first and second hydrogen-containing streams, each having an increased molar proportion of hydrogen compared to the reactant stream. The recovery assembly includes a shift conversion where the carbon monoxide of at least one carbon monoxide-containing stream is at least partially converted into hydrogen and carbon dioxide by reaction with steam to obtain a converted stream having hydrogen and carbon dioxide at least partially recycled to a hydrogen recovery from which the first and second hydrogen-containing streams are obtained. A nitrogen stream and, at least partially, the first hydrogen-containing stream are supplied to an ammonia reactor assembly for at least partial conversion into ammonia and, at least partially, the second hydrogen-containing stream is supplied to a methanol reactor assembly for at least partial conversion into the methanol.

BACKGROUND

Various approaches for combined production of methanol and ammonia are known from the prior art. The laid-open publication DE 10 2004 013 539 A1, on which the present disclosure is based, describes a process for the co-production of methanol and ammonia from natural gas. A synthesis gas is obtained from the natural gas by catalytic partial oxidation and is supplied to various reactor assemblies in the process sequence, which are arranged in parallel, for the methanol synthesis and the ammonia synthesis. In particular, a water-gas shift reaction is carried out downstream of the synthesis gas reactor for the partial conversion of carbon monoxide into carbon dioxide and hydrogen, followed by the substantially complete washing out of the carbon dioxide in an absorber. The resulting gas mixture is then divided into two streams and supplied to a methanol synthesis and an ammonia synthesis. The disadvantage of this prior art is that by splitting the streams in the absorber, a composition of the gas mixture must be achieved which, at any rate, must be suitable as starting gas equally for the methanol synthesis and ammonia synthesis. Apart from the supply of a residual gas from a low-temperature decomposition prior to the methanol synthesis for the ammonia synthesis, there is no possibility in this process to cause a shift of the gas composition between the ammonia path and the methanol path. As a result, very narrow boundary conditions have to be applied with regard to the gas compositions.

SUMMARY

Proceeding from this prior art, the object of the disclosure is therefore to create the possibility of a more flexible adjustment of process parameters in the combined production of methanol and ammonia by coupling the methanol and ammonia paths.

With regard to a process for combined production of methanol and ammonia having the features of the preamble of claim 1, this object is achieved by the features of the characterising part of claim 1. With regard to a plant for combined production of methanol and ammonia, this problem is achieved by the features of the characterising part of claim 15.

The disclosure is based on the finding that the step for increasing the hydrogen yield and for the effective removal of carbon oxides with respect to the ammonia synthesis by shift conversion and subsequent hydrogen recovery can be applied, at least partially, also to a residual gas stream of the methanol reactor assembly. This is because, firstly, the hydrogen-intensive carbon dioxide produced during methanol synthesis is removed from the methanol synthesis cycle, since hydrogen recovery is accompanied by an at least partial removal of the carbon dioxide, and therefore the process consumes less hydrogen overall. Secondly, the additional hydrogen recovered during shift conversion is returned to the methanol synthesis, which also improves stoichiometry. Since the corresponding supply and discharge rates can also be dynamically varied in a simple way, this results in additional degrees of freedom for better process control.

In the process for combined production of methanol and ammonia according to the disclosure, a reactant carbon monoxide-containing stream is supplied to a recovery assembly for obtaining a first hydrogen-containing stream and a second hydrogen-containing stream, each with an increased molar proportion of hydrogen compared with the reactant stream, wherein the recovery assembly comprises a shift conversion, in which shift conversion carbon monoxide of at least one carbon monoxide-containing stream is at least partially converted into hydrogen and carbon dioxide by reaction with steam so as to obtain a converted stream comprising hydrogen and carbon dioxide, which converted stream is at least partially supplied to a hydrogen recovery, from which hydrogen recovery the first hydra gen-containing stream and the second hydrogen-containing stream are recovered, wherein a nitrogen stream and, at least partially, the first hydrogen-containing stream are supplied to an ammonia reactor assembly for at least partial conversion into ammonia, and wherein, at least partially, the second hydrogen-containing stream is supplied to a methanol reactor assembly for at least partial conversion into methanol. In addition to carbon monoxide, the reactant stream may also contain further constituents such as hydrogen and carbon dioxide. The converted stream may also contain other components besides hydrogen and carbon dioxide. The first hydrogen-containing stream can correspond in its composition to the second hydrogen-containing stream. However, the two hydrogen-containing streams can also have different compositions and also different molar proportions of hydrogen.

The process according to the disclosure is characterised in that the reactant stream comprises a residual gas stream with unreacted carbon oxides from the methanol reactor assembly. This residual gas stream is thus a gas stream which, with regard to the process sequence, has already passed upstream through a methanol reactor for the synthesis of methanol, which is included in the methanol reactor assembly, and which gas stream contains carbon oxides which were not converted into methanol in the methanol reactor. It is preferable that the residual gas stream is branched off from the methanol reactor assembly adjustably in respect of its mass flow. Such an adjustment may also allow the ratio between methanol produced and ammonia produced to be varied. It may also be the case that the residual gas stream has undergone an intermediate treatment, for example a condensation, after leaving the methanol reactor. The reactant stream can comprise other gas streams in addition to the residual gas stream, or alternatively can include the residual gas stream. It is possible that an increase in the molar proportion of hydrogen means an increase in the molar proportion of hydrogen in relation to the hydrogen and carbon oxides. Consequently, an increase in the molar proportion of hydrogen would also occur if carbon oxides were removed but the molar proportion of hydrogen in the stream as a whole were to remain the same or even decrease by supply of another substance without carbon oxides. The ammonia reactor assembly preferably comprises an ammonia synthesis compressor which is set up to increase the pressure of the nitrogen stream and of the first hydrogen-containing stream supplied to the ammonia reactor assembly.

In principle, the reactant stream can be supplied to the recovery assembly at any point in the process sequence. It is preferable that the reactant stream is supplied to the shift conversion. This can also be expressed by the fact that the at least one carbon monoxide-containing stream comprises the reactant stream. However, it is also possible that the reactant stream is only used in particular for hydrogen recovery. In this case, within the process sequence, the reactant stream can either be combined with the converted stream upstream of the hydrogen recovery or can be supplied to the hydrogen recovery process separately to the converted stream. Finally, it is also possible that one part of the reactant stream is supplied to the shift conversion and another part of the reactant stream is supplied only to hydrogen recovery, these parts of the reactant stream also possibly being adjustable in respect of their absolute or relative amount of substance.

In principle, the shift conversion can comprise a single conversion step for shift conversion. The term "shift conversion" in this case always refers to a reactor for the water-gas shift reaction known from the prior aft, in which carbon monoxide and steam are converted into carbon dioxide and hydrogen. A preferred embodiment of the process is characterised in that the shift conversion has a first conversion stage for shift conversion and a second conversion stage for shift conversion downstream of the first conversion stage in the process sequence, and in that the shift conversion in the first and second conversion stages takes place at a different temperature, so that the chemical equilibrium in the first conversion stage is different from the chemical equilibrium in the second conversion stage. In this way, the water-gas shift reaction can be provided in both a high temperature and a low temperature range, whereby a sufficiently low concentration of carbon monoxide can be achieved within an acceptable time. It may be that the reactant stream is supplied to the first conversion stage.

It is also known from the prior art that the chemical equilibrium and the kinetics of the water-gas shift reaction are temperature-dependent. Consequently, the kinetics in the first conversion stage differ from the kinetics in the second conversion stage. According to this embodiment, the shift conversion can also have more than two conversion stages.

Another preferred embodiment of the process is characterised in that a further reactant carbon monoxide-containing stream is supplied to the recovery assembly. In particular, it is possible that the further reactant stream is supplied to the shift conversion for at least partial conversion into hydrogen and carbon dioxide by reaction with steam. Then, the at least one carbon monoxide-containing stream comprises the further reactant stream. In this way, the adjustability of the overall process can be increased further still. This further reactant stream can be combined with the first-mentioned reactant stream within the shift conversion. In the case of a plurality of conversion stages, the further reactant stream can be supplied to the shift conversion in the process sequence at a point which differs from the supply of the reactant stream.

It is particularly preferred here that the reactant stream is supplied to the shift conversion downstream of the first conversion stage in the process sequence and upstream of the second conversion stage in the process sequence. It is then preferred that the further reactant stream is supplied to the first conversion stage. In this way, the reactant stream and the further reactant stream each pass through different numbers of conversion steps of the shift conversion. Since the reactant stream comprises the residual gas stream from the methanol synthesis, this can often have a lower proportion of carbon monoxide than the further reactant stream. In such a case, an upstream shift conversion in the high temperature range may be useful for the further reactant stream, but is not necessary for the reactant stream with the residual gas.

According to a preferred embodiment of the process it is intended that at least 80%, preferably at least 85% and in Particular at least 90% of the molar proportion of carbon monoxide of the reactant stream, in particular also of the further reactant stream, is converted in the shift conversion into hydrogen and carbon dioxide by reaction with steam.

A preferred embodiment of the process is characterised in that the shift conversion comprises a low-temperature shift conversion stage, in which substantially only a low-temperature water-gas shift reaction takes place. It is preferred that this water-gas shift reaction takes place at less than 300° C. In particular, the second conversion stage may be the low-temperature shift conversion stage. At low temperature the kinetics are slower, but the chemical equilibrium is at a lower concentration of carbon monoxide. Consequently, the low-temperature shift reaction can be used to achieve an extensive conversion of remaining amounts of residual carbon monoxide in the reactant stream.

A further preferred embodiment of the process is characterised in that the shift conversion comprises a high-temperature shift conversion stage in which substantially exclusively a high-temperature water-gas shift reaction—preferably at Least at 300° C.—takes place. In particular, it may be that the first conversion stage is the high-temperature shift conversion stage. Due to the better kinetics at higher temperatures, a rapid reduction of the carbon monoxide concentration to a lower level can be achieved in this first stage, especially if this concentration is initially rather high.

According to a preferred embodiment of the process it is provided that, within the process sequence, a synthesis gas stream comprising hydrogen and carbon oxides is supplied to the methanol reactor assembly upstream of the shift conversion for at least partial conversion into methanol, and therefore the unreacted carbon oxides originate from the synthesis gas stream. This upstream arrangement in relation to the shift conversion in the process sequence means that this synthesis gas stream has not yet undergone the shift conversion when it is supplied to the methanol reactor assembly. With fresh synthesis gas it is often not necessary or useful to carry out a shift conversion already before the methanol synthesis. This is because the aim may be to have as much carbon monoxide as possible available for a first reactor stage of the methanol synthesis. Preferably, the methanol reactor assembly comprises a synthesis gas compressor to increase the pressure of the synthesis gas stream.

With regard to the second hydrogen-containing stream from the hydrogen recovery, it is preferred that this is combined with the synthesis gas stream. This allows the desired stoichiometric number to be set. In particular, it is possible that the second hydrogen-containing stream is supplied to the synthesis gas stream upstream of the synthesis gas compressor in the process sequence.

In this regard, it is further preferred that the methanol reactor assembly comprises a condensation stage to separate methanol and maintain the residual gas stream. Besides methanol, water can also be separated in the condensation stage. After separation of the methanol, such a residual gas stream regularly has a significantly reduced proportion of carbon monoxide compared to the stream supplied to the methanol reactor assembly. Furthermore, in addition to the residual gas stream, a recycle stream from the condensation stage can also be obtained, preferably with a composition corresponding to the residual gas stream, and is recycled in particular for at least partial conversion into methanol.

A preferred embodiment of the process is characterised in that the methanol reactor assembly comprises a first and a second reactor stage for the synthesis of methanol, in that the synthesis gas stream is supplied to the first reactor stage, and in that a further residual gas stream is supplied with unreacted carbon oxides from the first reactor stage to the second reactor stage. Consequently, not all of the residual gas from the methanol synthesis as a whole and not all of the residual gas from the first reactor stage is supplied to the shift conversion. It is preferred that the methanol reactor assembly comprises an intermediate compressor for increasing the pressure of the further residual gas stream before supplying the further residual gas stream to the second reactor stage.

Here it is further preferred that a mass flow of the residual gas stream is adjustable. Alternatively or additionally, it is possible that a residual gas of the first reactor stage is variably divided into the residual gas stream and the further residual gas stream. Regarding the above-mentioned condensation stage, it is preferred that the condensation stage is arranged between the first and the second reactor stage within the process, and that the residual gas stream and the further residual gas stream, as well as, where applicable, the recycle stream is obtained from the condensation stage.

Furthermore, it is possible that the second reactor stage may be followed within the process by a further condensation stage for the separation of methanol and for obtaining the recycle stream. It is then preferable to return the recycle stream to the first reactor stage and thus to recycle it.

In principle, the above-mentioned synthesis gas stream can be obtained in any way and can originate from any source. Another preferred embodiment of the process is especially characterised by the fact that a carbon-containing energy carrier stream is supplied to a synthesis gas reactor assembly in order to obtain the synthesis gas stream. Here it is further preferred that the further reactant stream is a further synthesis gas stream comprising hydrogen and carbon oxides obtained from the synthesis gas reactor assembly. In such a case, not only is the reactant stream with residual gas from the methanol synthesis supplied to the shift conversion, but also fresh synthesis gas. In this way, the ratio of hydrogen to carbon oxides can be further increased. Here it is preferred that the further synthesis gas stream is branched off adjustably in respect of its mass flow from the synthesis gas reactor assembly. The ratio between methanol produced and ammonia produced can also be varied by this adjustment.

With regard to the synthesis gas reactor, a large number of variants is also possible in principle. One of the preferred variants provides that an oxygen-containing stream is supplied to the synthesis gas reactor assembly and that in a reactor of the synthesis gas reactor assembly synthesis gas is obtained for the synthesis gas stream, in particular also for the further synthesis gas stream, by a catalytic partial oxidation by means of the oxygen-containing stream. Firstly, this offers the advantage that the synthesis gas can be provided at a higher pressure than in a conventional steam reforming. It is preferable that the oxygen-containing stream comprises mainly and in particular substantially entirely oxygen. Compared to the use of ambient air for catalytic partial oxidation, this leads to a smaller volume of process gas due to the extensive or substantially complete absence of nitrogen, which in turn allows a smaller and thus more favourable dimensioning of the downstream equipment, such as the compressors. As an alternative or in addition to catalytic partial oxidation, it may be possible to obtain synthesis gas for the synthesis gas stream by steam reforming in an optional further reactor of the synthesis gas reactor assembly.

It may be that the synthesis gas reactor assembly has a pre-reformer, upstream of the partial catalytic oxidation, for splitting hydrocarbons with at least two hydrocarbons.

In accordance with a preferred embodiment of the process, is provided that the synthesis gas reactor assembly, within the process sequence, has a multi-stage waste heat utilisation downstream of the reactor for recovering heat from the obtained synthesis gas stream and that the synthesis gas stream and the further synthesis gas stream are obtained after different stages of the waste heat utilisation. The synthesis gas is regularly obtained from a synthesis gas reactor at a temperature which is too high for further processing. For this reason, a waste heat utilisation can be provided, which for example comprises a waste heat boiler for the production of process steam as well as one or more heat exchangers and thus both cools the synthesis gas and produces process steam or provides heating at another point in the process sequence. Preferably, a first stage of the waste heat utilisation comprises the waste heat boiler and a downstream stage comprises a heat exchanger. It may be that for methanol synthesis the synthesis gas has to be cooled to a lower temperature than required for shift conversion and especially for a high-temperature shift conversion stage.

Here it is preferred that the further synthesis gas stream is branched off upstream of the synthesis gas stream in the process sequence. In this way, the further synthesis gas stream has a higher temperature than the synthesis gas stream when it is branched off. Here it is preferred that the further synthesis gas stream is branched off from the waste heat utilisation adjustably in respect of its mass flow. This also makes it possible to vary the ratio between methanol produced and ammonia produced.

A preferred embodiment of the process is characterised in that the nitrogen stream is obtained from an air separation unit for the recovery of molecular oxygen from the ambient air. Furthermore, it is preferred that the oxygen-containing stream is an oxygen stream obtained from the air separation, in particular comprising substantially oxygen. In this way, the oxygen produced during the air separation to obtain the nitrogen stream can be used advantageously for the production of the synthesis gas.

Another preferred embodiment of the process is characterised in that a purge gas with carbon dioxide is obtained from the hydrogen recovery. Preferably, this purge gas has an increased proportion of carbon dioxide compared to the converted stream. It may also be that this purge gas comprises substantially carbon dioxide. This carbon dioxide can also be supplied to a use, for example for the production of urea. It may be that more than one stream of purge gas is obtained from the hydrogen recovery process, it then being possible for the carbon dioxide to be enriched in one of the streams of purge gas, and for substantially other components such as noble gas residues to be enriched in another stream of the purge gas. This other stream can then be used, for example, as fuel gas for underfiring in a furnace.

In principle, it is possible that residues of carbon dioxide remain in the first hydrogen-containing stream or in the second hydrogen-containing stream. However, it is preferred that in the hydrogen recovery substantially all carbon dioxide of the converted stream is removed, so that the first and/or the second hydrogen-containing stream is substantially free of carbon dioxide.

In principle, the above removal of carbon dioxide from the converted stream can be achieved in any way. Another preferred embodiment of the process is characterised in that the hydrogen recovery comprises a carbon dioxide scrubber for at least partial washing of the carbon dioxide out of the converted stream by means of a washing agent. It is possible that only an (in particular) adjustable part of the converted stream is supplied to the carbon dioxide scrubber. It is preferable that the purge gas is at least partially obtained from the carbon dioxide scrubber. It may also be that the second hydrogen-containing stream is obtained from the carbon dioxide scrubber by washing the carbon dioxide out of the converted stream. Since the second hydrogen-containing stream is supplied to the methanol synthesis, it often requires a lower purity than the first hydrogen-containing stream supplied to the ammonia synthesis.

According to a preferred embodiment of the process, it is provided that the hydrogen recovery comprises a pressure swing adsorption (PSA) plant for recovering the first hydrogen-containing stream, preferably also for obtaining the second hydrogen-containing stream. This pressure swing adsorption plant can be arranged downstream of the carbon dioxide scrubber in the process sequence. It is possible that the pressure swing adsorption plant has a multi-stage pressure swing adsorption device. It is also possible that the first hydrogen-containing stream comprises substantially hydrogen and is free of carbon oxide. This allows, especially when supplying pure nitrogen for ammonia synthesis, a smaller dimensioning of the reactor for ammonia synthesis and all components for recycling. It is also possible that the second hydrogen-containing stream comprises substantially hydrogen and is substantially free of carbon oxide.

It is also possible that the hydrogen recovery has a device for methanising the converted stream. Especially in this methanisation, carbon dioxide and carbon monoxide are converted into methane. In combination with the shift conversion, such methanisation also means an increase in the molar proportion of hydrogen, particularly by reducing the molar proportion of carbon oxides and the formation of additional hydrogen in the shift conversion. In this way, carbon oxides can be prevented from entering the ammonia reactor assembly.

The plant according to the disclosure is used for the combined production of methanol and ammonia and comprises a recovery assembly, to which a reactant stream with carbon monoxide is supplied and from which a first hydrogen-containing stream and a second hydrogen-containing stream are obtained, each with an increased molar proportion of hydrogen compared with the reactant stream, the recovery assembly comprising a shift conversion, in which carbon monoxide of at least one carbon monoxide-containing stream is at least partially converted into hydrogen and carbon dioxide by reaction with steam, such that a converted stream comprising hydrogen and carbon dioxide is obtained, and also comprising a hydrogen recovery, to which the converted stream is at least partially supplied and from which the first hydrogen-containing stream and the second hydrogen-containing stream are obtained. The plant according to the disclosure also comprises an ammonia reactor assembly, to which a nitrogen stream and at least part of the first hydrogen-containing stream are supplied for at least partial conversion into ammonia, and a methanol reactor assembly, to which the second hydrogen-containing stream is at least partially supplied for at least partial conversion into methanol.

The plant according to the disclosure is characterised in that the reactant stream comprises a residual gas stream with unreacted carbon oxides from the methanol reactor assembly.

Preferred embodiments and features of the plant according to the disclosure correspond to preferred embodiments and features of the process according to the disclosure, and vice versa.

BRIEF DESCRIPTION OF THE DRAWINGS

Further details, features, objectives and advantages of the present disclosure are explained below on the basis of drawings which show merely exemplary embodiments. In the drawings.

DETAILED DESCRIPTION OF THE DRAWINGS

Figure 1:
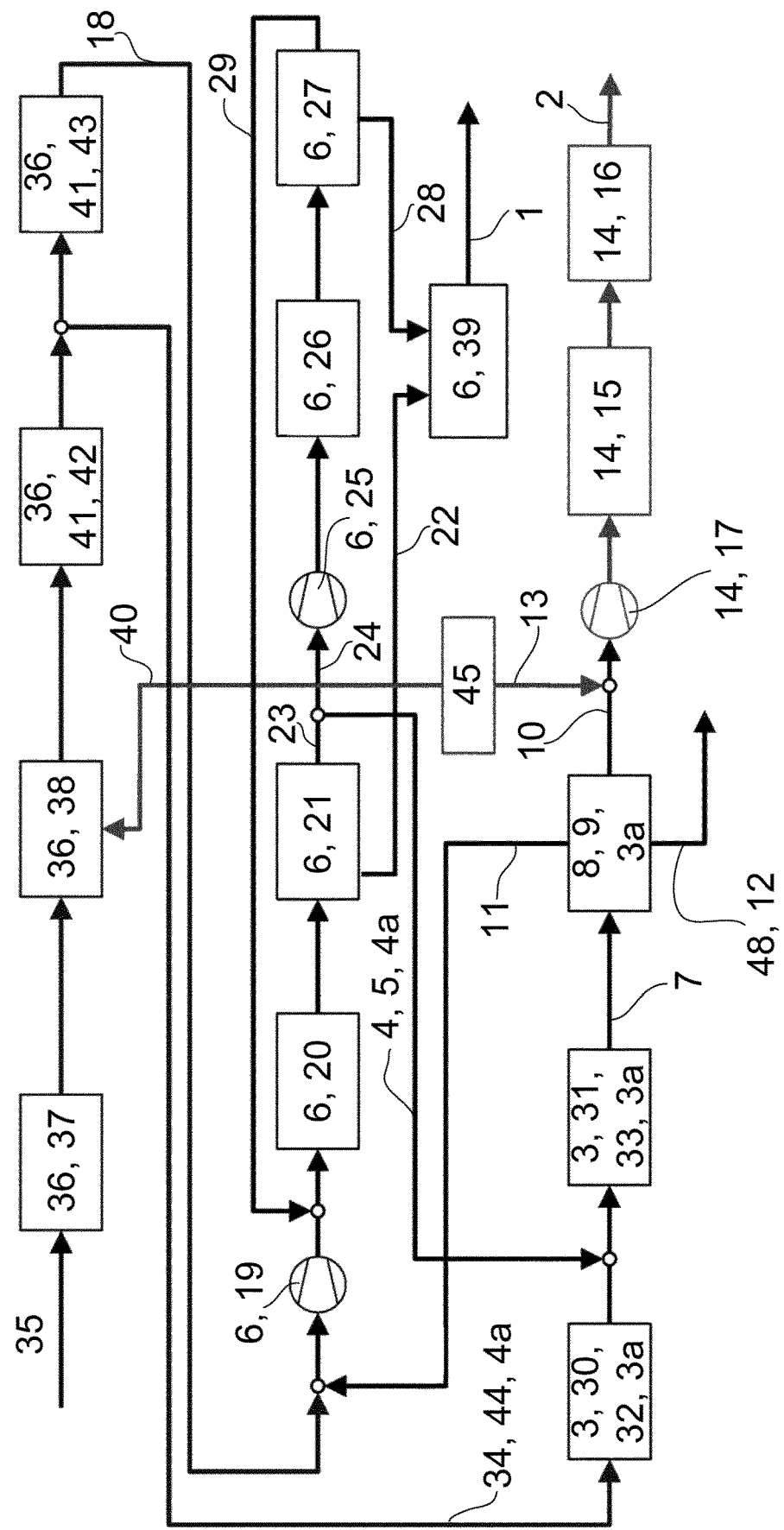
FIG. 1 shows a schematic illustration of a first exemplary embodiment of the proposed plant for carrying out the proposed process.

The proposed plant for combined production of methanol 1 and ammonia 2 shown in FIG. 1 in accordance with a first exemplary embodiment comprises a recovery assembly 3a with a shift conversion 3, to which a reactant stream 4 is supplied as a carbon monoxide-containing stream 4a. The reactant stream 4 is a residual gas stream 5 with unreacted carbon oxides from a methanol reactor assembly 6 of the proposed plant which is used for the production of methanol 1 by synthesis.

From the shift conversion 3, converted stream 7 is obtained, which contains hydrogen and carbon dioxide. In particular, the water-gas shift reaction in the shift conversion 3 largely converts the carbon monoxide of the reactant stream 4 with steam into hydrogen and carbon dioxide. This converted stream 7 is supplied to a hydrogen recovery 8 of the recovery assembly 3a, which in this case is a pressure swing adsorption plant 9. From this, a first hydrogen-containing stream 10 and a second hydrogen-containing stream 11 are obtained, both of which comprise substantially hydrogen. In addition, a purge gas 12 comprising an off-gas 48 of the hydrogen recovery 8 is obtained, which purge gas 12 comprises the residual stream of the converted stream 7 after separation of the first hydrogen-containing stream 10 and the second hydrogen-containing stream 11.

The first hydrogen-containing stream 10 is combined with a nitrogen stream 13 and supplied with this to an ammonia reactor assembly 14 for the synthesis of ammonia 2. The ammonia reactor assembly 14 comprises an ammonia reactor 15, in which the conversion of hydrogen and nitrogen into ammonia 2 takes place, as well as a separation stage 16 arranged downstream in the process sequence for separating the ammonia 2, and an ammonia synthesis compressor 17 arranged upstream in the process sequence for increasing the pressure.

The second hydrogen-containing stream 11 is supplied to the methanol reactor assembly 6 together with a synthesis gas stream 18 comprising substantially hydrogen and carbon oxides. This comprises a synthesis gas compressor 19 for increasing the pressure of the synthesis gas stream 18 and of the second hydrogen-containing stream 11 which is combined with it. Arranged downstream of the synthesis gas compressor 19 in the process sequence is a first reactor stage 20 for the synthesis of methanol 1 of the methanol reactor assembly 6, which is followed in the process sequence by a condensation stage 21, likewise comprised by the methanol reactor assembly 6, for the separation of methanol and water in a raw methanol stream 22. The separated raw methanol stream 22 is supplied to a distillation stage 39 of the methanol reactor assembly 6, from which methanol 1 is then obtained. It would also be conceivable to supply the second hydrogen-containing stream 11 of the methanol reactor assembly 6 downstream of the synthesis gas compressor 19 in the process sequence.

A residual gas 23 with the unreacted gas components from the first reactor stage 20 is also obtained from the condensation stage 21, which residual gas 23 is divided into the residual gas stream 5 for supplying to the shift conversion 3 and into a further residual gas stream 24, which further residual gas stream 24 is supplied to a second reactor stage 26 after pressure increase by an intermediate compressor 25. This division into the residual gas stream 5 and into the further residual gas stream 24 is variable. The second reactor stage is followed in the process sequence by a further condensation stage 27, from which a further raw methanol stream 28 is obtained, which is also supplied to the distillation stage 39. Residual gas from the further condensation stage 27 is returned to the first reactor stage 20 as a recycle stream 29. The intermediate compressor 25, the second reactor stage 26 and the further condensation stage 27 are also comprised by the methanol reactor assembly 6.

The shift conversion 3 comprises firstly a high-temperature shift conversion stage 30, in which a high-temperature water-gas shift reaction takes place at least at 300° C., and a low-temperature shift conversion stage 31 arranged downstream in the process sequence, in which a low-temperature water-gas shift reaction takes place at less than 300° C. It follows that the particular chemical equilibrium is also different. The high-temperature shift conversion stage 30 is therefore a first conversion stage 32 for shift conversion, and the low-temperature shift conversion stage 31 is a second conversion stage 33 for shift conversion, downstream of the first conversion stage 32 in the process sequence. The reactant stream 4 is supplied here in the process sequence to the shift conversion 3 between the high-temperature shift conversion stage 30 and the low-temperature shift conversion stage 31, so that the reactant stream 4 only passes through the low-temperature shift conversion stage 31.

A further reactant stream 34 is also supplied as a further carbon monoxide-containing stream 4a to the shift conversion and here especially to the high-temperature shift conversion stage 30, so that it then also passes through the low-temperature shift conversion stage 31.

This further additional reactant stream 34 is taken from the arrangement for providing synthesis gas described below, which also provides the synthesis gas stream 18. More specifically, a carbon-containing energy carrier stream 35, which in this case is a natural gas stream, is supplied to a synthesis gas reactor assembly 36. In particular, the carbon-containing energy carrier stream 35 is first supplied to a pre-reformer 37 of the synthesis gas reactor assembly 36, in which pre-reformer 37 higher hydrocarbons are split. It is then supplied to a reactor 38 of the synthesis gas reactor assembly 36 for catalytic partial oxidation. For this catalytic partial oxidation, an oxygen-containing stream 40 is supplied to the reactor 38, which is a stream comprising substantially oxygen.

Downstream of the reactor 38 there is a two-stage waste heat utilisation 41 of the synthesis gas reactor assembly 36, which is intended to cool the synthesis gas on the one hand and to recover the heat on the other. The waste heat utilisation 41 comprises a waste heat boiler 42 for generating process steam and a heat exchanger arrangement 43 having several individual heat exchangers downstream of the waste heat boiler 42 in the process sequence. The further reactant stream 34 is branched off as a further synthesis gas stream 44 downstream of the waste heat boiler 42 in the process sequence, whereas the synthesis gas stream 18 is obtained after passing through the heat exchanger arrangement 43. The amount of synthesis gas branched off as a further synthesis gas stream 44 is adjustable. Due to this upstream branching, the further synthesis gas stream 44 has a higher temperature than the synthesis gas stream 18, which is advantageous in light of its supply to the high-temperature shift conversion stage 30.

The oxygen-containing stream 40 comes from an air separation unit 45, which also provides the nitrogen stream 13.

In the first exemplary embodiment, the energy carrier stream 35 has a mass flow of 175 t/h, the synthesis gas from the reactor 38 has a mass flow of 630 t/h, the further reactant stream 34 has a mass flow of 190 t/h, the synthesis gas stream 18 has a mass flow of 440 t/h, the methanol 1 has a mass flow of 210 t/h, and the ammonia 2 has a mass flow of 70 t/h. It should be noted that water and steam are supplied, especially upstream of the reactor 38 in the process sequence.

For the further exemplary embodiments in FIGS. 2 to 6, only the differences from the first exemplary embodiment or from another exemplary embodiment are described. Unless otherwise stated, they correspond to the particular exemplary embodiment serving as a starting point.

Figure 2:
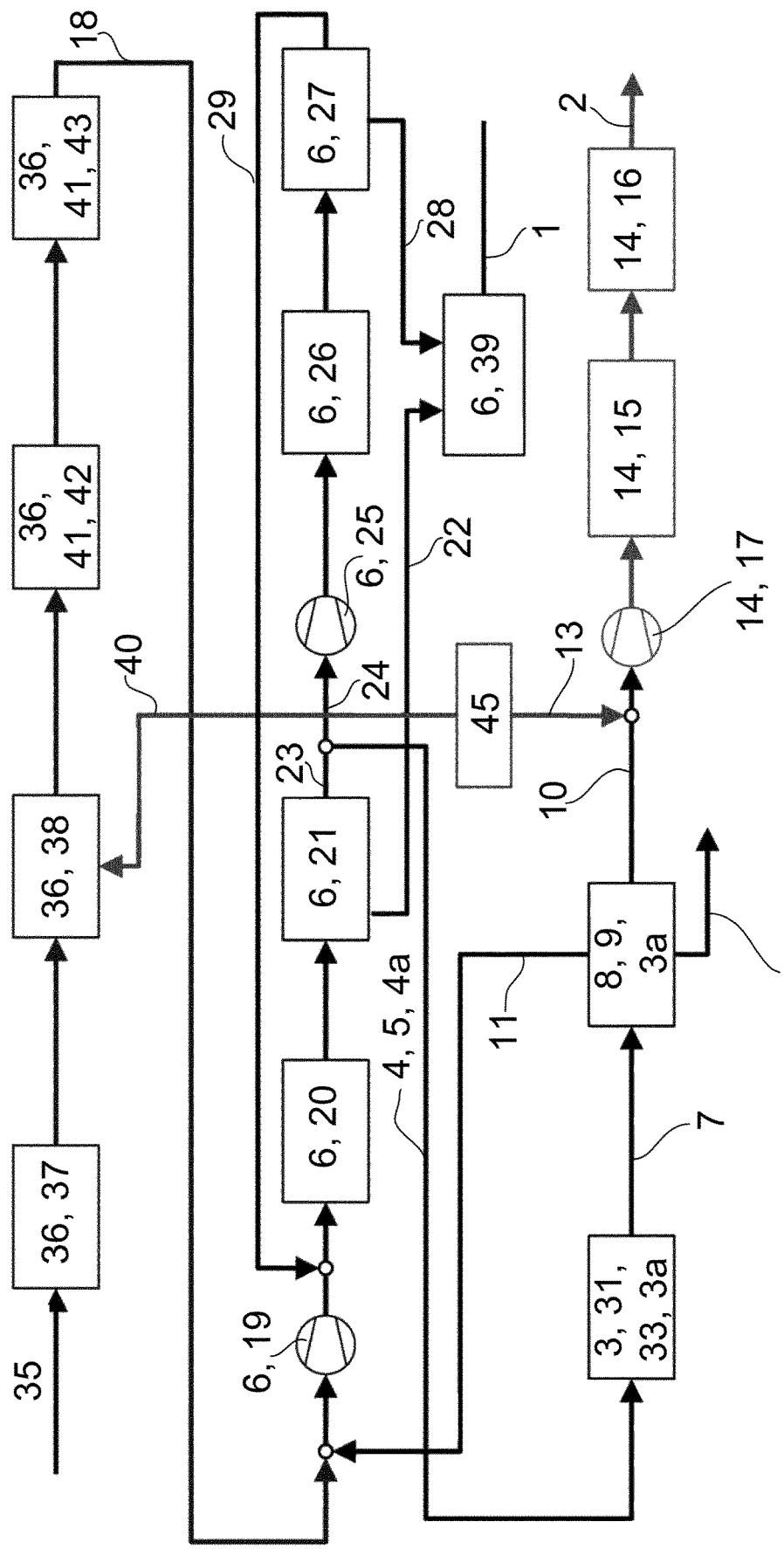
FIG. 2 shows a schematic illustration of a second exemplary embodiment of the proposed plant for carrying out the proposed process.

The second exemplary embodiment in FIG. 2 differs from the first exemplary embodiment in that the further reactant stream 44 is omitted. Accordingly, the shift conversion 3 is single-stage and has only a low-temperature shift conversion stage 31.

The third exemplary embodiment in FIG. 3 again proceeds from the first exemplary embodiment. Here, however, the hydrogen recovery 8 additionally has a carbon dioxide scrubber 46, to which a variable part of the converted stream 7 is supplied. From this part the carbon dioxide is substantially completely washed out by a washing agent and recovered in a CO2 stream 49 comprising substantially carbon dioxide. The bypassed part of the converted stream. 7 as well as the converted stream 7 after the washing is supplied to the pressure swing adsorption plant 9, wherein the already reduced molar proportion of carbon dioxide reduces the load of the pressure swing adsorption plant 9. The purge gas 12 here comprises both the off-gas 48 from the pressure swing adsorption plant 9 and the CO2 stream 49 from the carbon dioxide scrubber 46, and this can be supplied to a separate further processing.

Figure 3:
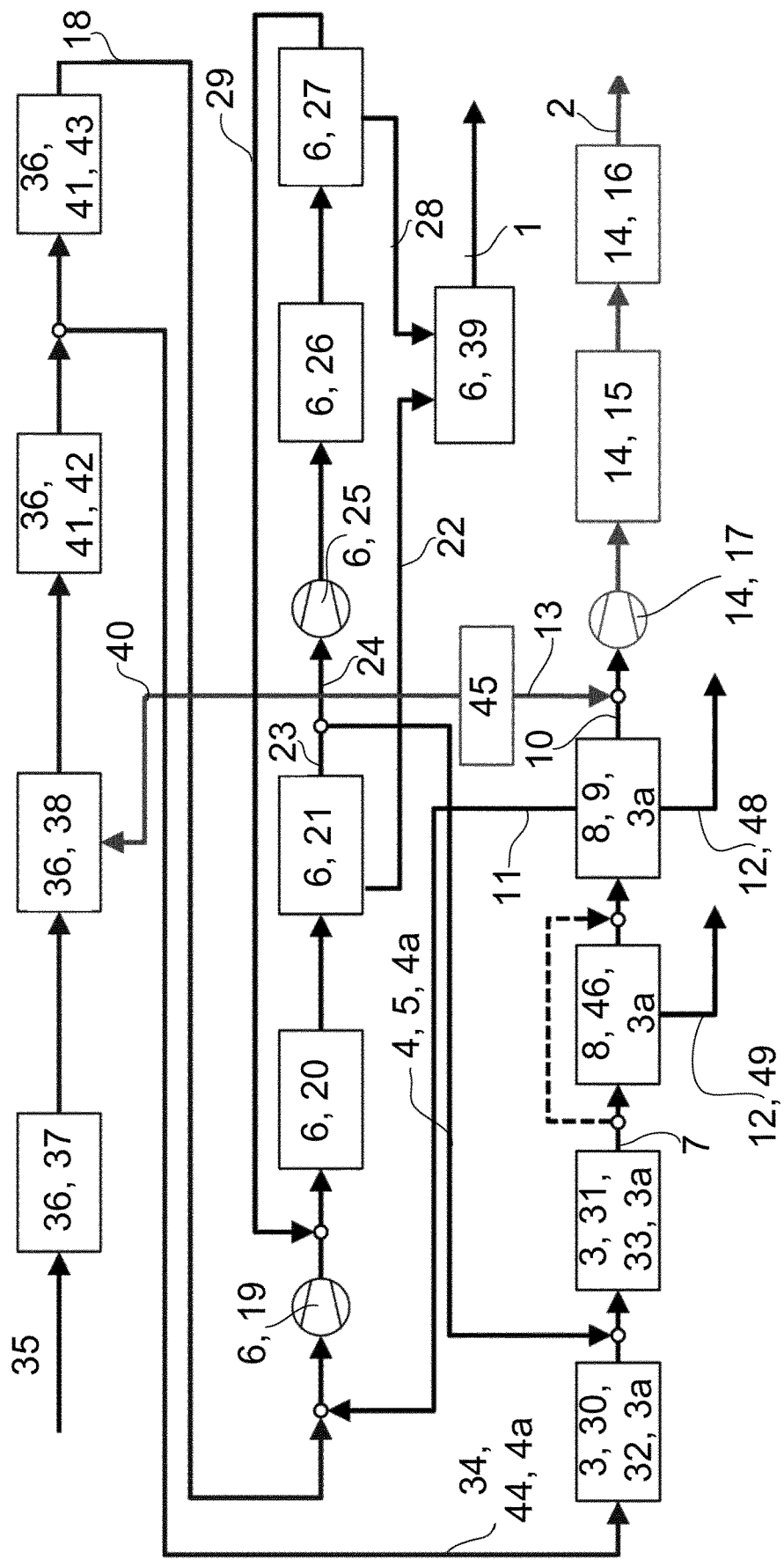
FIG. 3 shows a schematic illustration of a third exemplary embodiment of the proposed plant for carrying out the proposed process.
Figure 4:
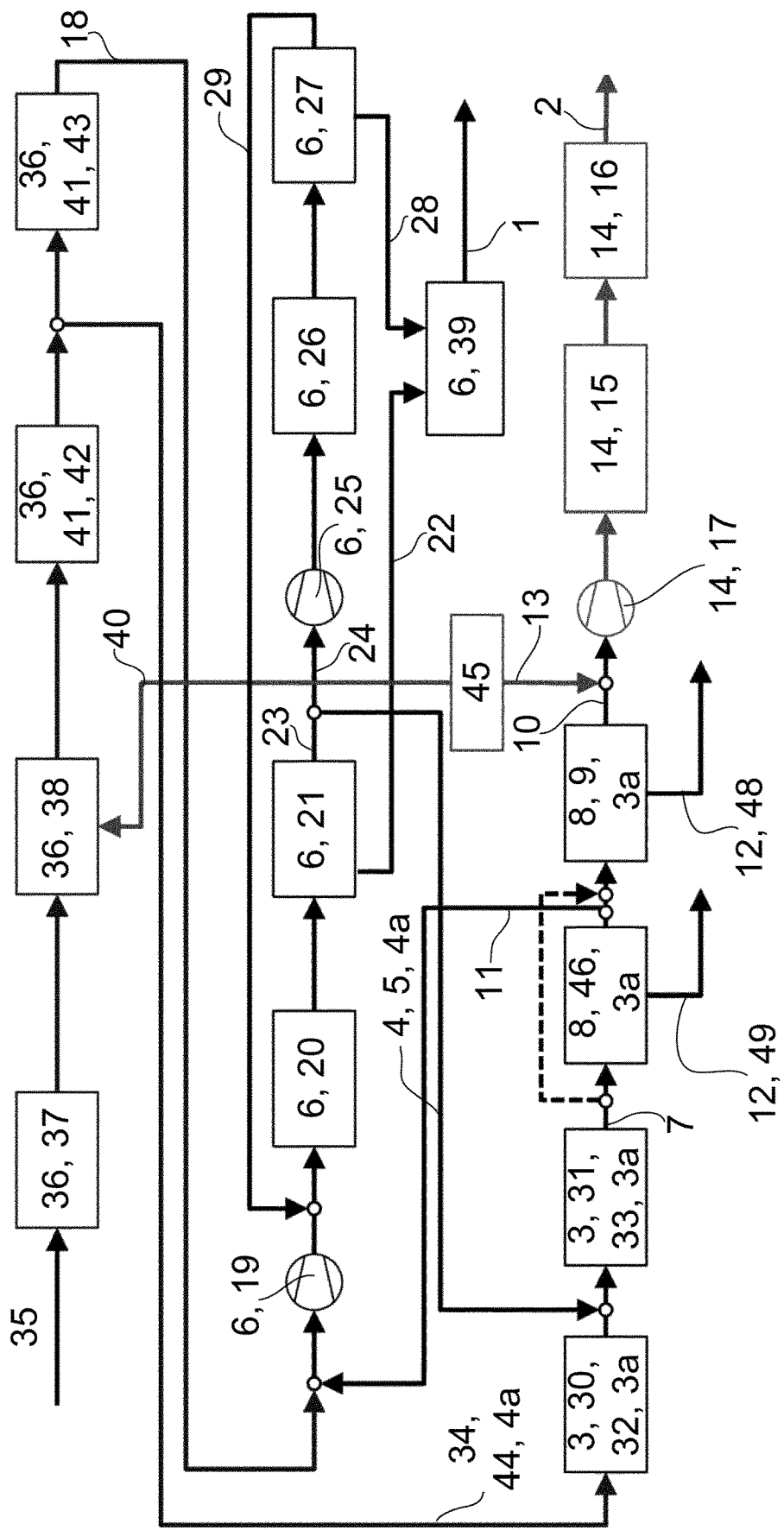
FIG. 4 shows a schematic illustration of a fourth exemplary embodiment of the proposed plant for carrying out the proposed process.

The fourth exemplary embodiment in FIG. 4 proceeds from the third exemplary embodiment in FIG. 3 and differs in that the second hydrogen-containing stream 11 is obtained by branching it off downstream of the carbon dioxide scrubber in the process sequence. Contrary to the exemplary embodiments 1 to 3, this is then not a stream comprising substantially hydrogen, but merely a stream enriched with hydrogen by the washing out of the carbon dioxide in its molar proportion. Since, however, in particular remaining carbon monoxide can be used for the methanol synthesis, this is harmless. The first hydrogen-containing stream 10 is still obtained from the pressure swing adsorption plant 9 and comprises substantially hydrogen.

In the fourth exemplary embodiment, the energy carrier stream 35 has a mass flow of 225 t/h, the synthesis gas from the reactor 38 has a mass flow of 780 t/h, the further reactant stream 34 has a mass flow of 290 t/h, the synthesis gas stream 18 has a mass flow of 490 t/h, the CO2 stream 49 has a mass flow of 230 t/h, the methanol 1 has a mass flow of 210 t/h, and the ammonia 2 has a mass flow of 145 t/h.

Figure 5:
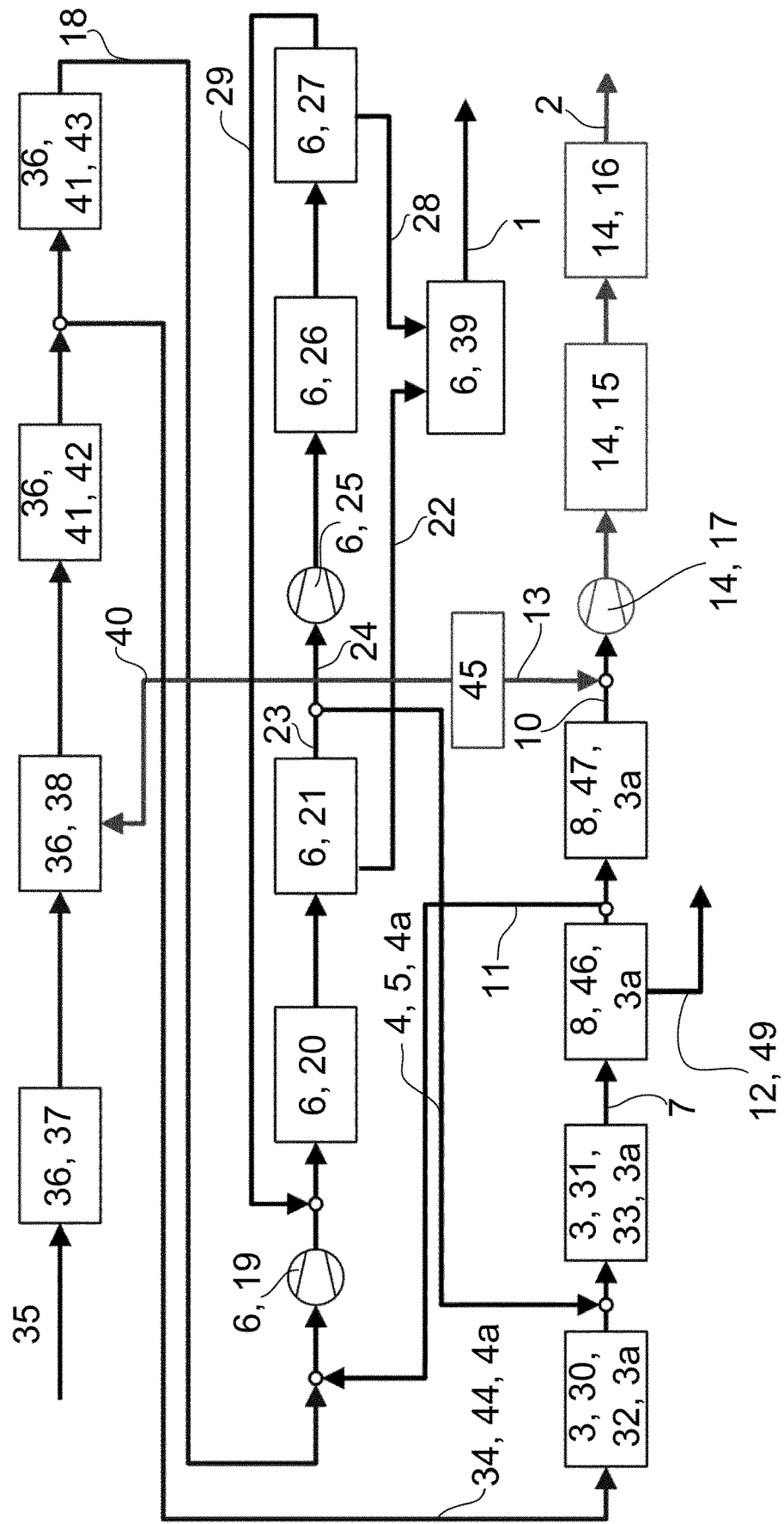
FIG. 5 is a schematic illustration of a fifth exemplary embodiment of the proposed plant for carrying out the proposed process.
Figure 6:
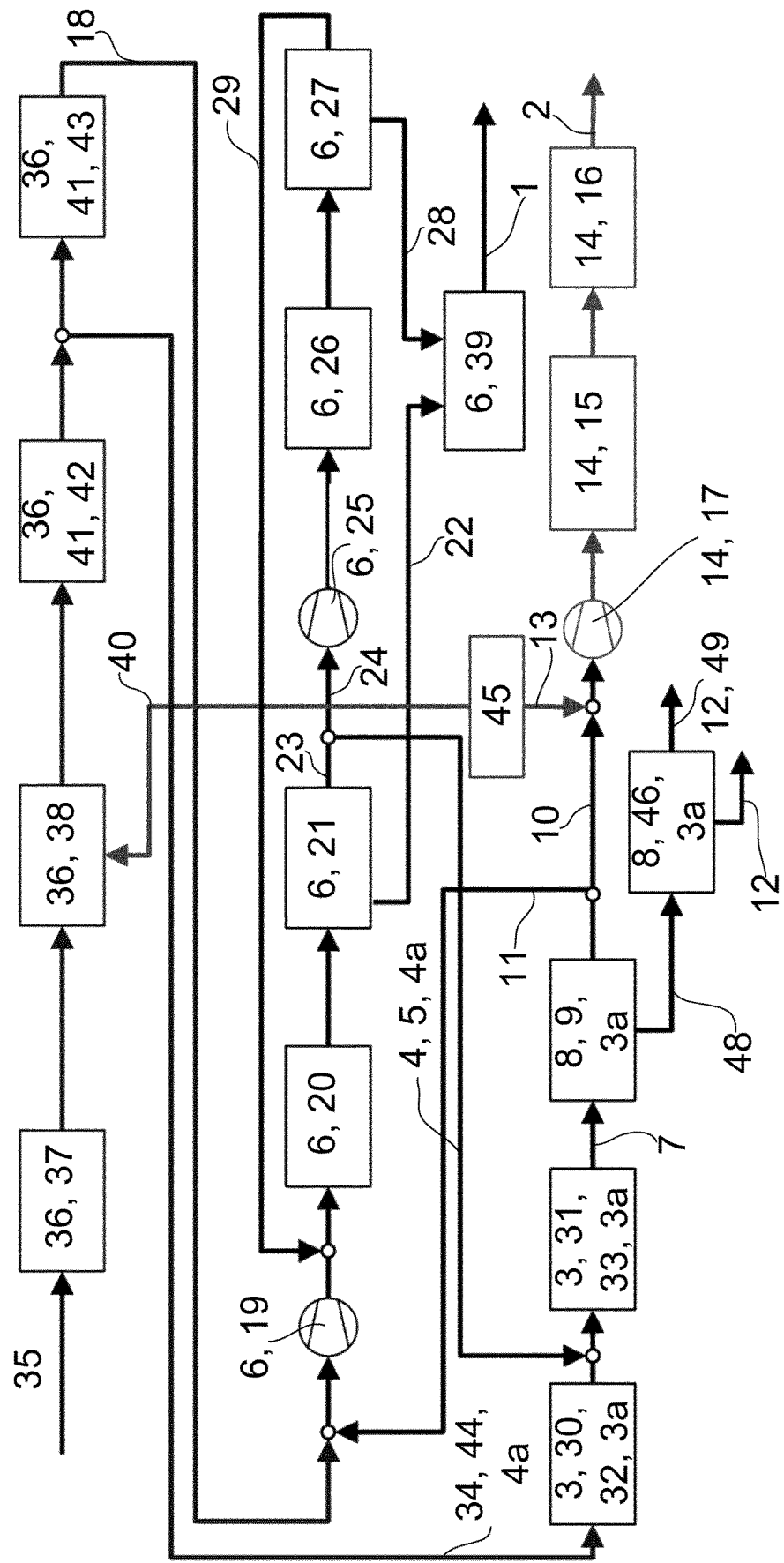
FIG. 6 is a schematic illustration of a sixth exemplary embodiment of the proposed plant for carrying out the proposed process.

The fifth exemplary embodiment of FIG. 5 proceeds from the fourth exemplary embodiment and differs firstly in that the entire converted stream 7 is supplied to the carbon dioxide scrubber 46. Secondly, instead of the pressure swing adsorption plant 9, the hydrogen recovery 8 has a device for methanising 47 the converted stream 7, from which the first hydrogen-containing stream 10 is obtained. Here the purge gas 12 comprises the CO2 stream 49.

Finally, the sixth exemplary embodiment in FIG. 6 again proceeds from the first exemplary embodiment and differs in that here the hydrogen recovery system 8 comprises a carbon dioxide scrubber 46, to which the off-gas 48 from the pressure swing adsorption system 9 is supplied. The purge gas 12 is obtained from the carbon dioxide scrubber 46, which includes the CO2 stream 49 in addition to the purge stream in the narrower sense.

The invention claimed is:

1. A process for combined production of methanol and ammonia, wherein a reactant stream comprising carbon monoxide is supplied to a recovery assembly to obtain a first hydrogen-containing stream and a second hydrogen-containing stream, each having an increased molar proportion of hydrogen compared to the reactant stream, wherein the recovery assembly comprises a shift conversion in which carbon monoxide of at least one carbon monoxide-containing stream is at least partially converted into hydrogen and carbon dioxide by reaction with steam to obtain a converted stream comprising hydrogen and carbon dioxide, which is at least partially supplied to a hydrogen recovery from which the first hydrogen-containing stream and the second hydrogen-containing stream are obtained, wherein a nitrogen stream and, at least partially, the first hydrogen-containing stream are supplied to an ammonia reactor assembly for at least partial conversion into ammonia and wherein, at least partially, the second hydrogen-containing stream is supplied to a methanol reactor assembly for at least partial conversion into methanol, wherein the reactant stream comprises a residual gas stream comprising unreacted carbon oxides from the methanol reactor assembly, wherein a synthesis gas stream comprising hydrogen and carbon oxides is supplied to the methanol reactor assembly upstream of the shift conversion in the process sequence for at least partial conversion into methanol, so that the unreacted carbon oxides originate from the synthesis gas stream, wherein a carbon-containing energy carrier stream is supplied to a synthesis gas reactor assembly for obtaining the synthesis gas stream, wherein the carbon-containing energy carrier stream is a natural gas stream.

2. The process according to claim 1, wherein the shift conversion comprises a first conversion stage for shift conversion and a second conversion stage or shift conversion, which is downstream of the first conversion stage in the process sequence, and in that the shift conversion in the first conversion stage and the second conversion stage takes place at a different temperature, and therefore the chemical equilibrium in the first conversion stage is different from the chemical equilibrium in the second conversion stage.

3. The process according to claim 2, wherein a further reactant stream comprising carbon monoxide is supplied to the recovery assembly, to the shift conversion for at least partial conversion into hydrogen and carbon dioxide by reaction with steam, wherein the reactant stream is supplied to the shift conversion downstream of the first conversion stage in the process sequence and upstream of the second conversion stage in the process sequence.

4. The process according to claim 1, wherein at least 80%, of the molar proportion of carbon monoxide of the reactant stream, is converted into hydrogen and carbon dioxide in the shift conversion by reaction with steam.

5. The process according to claim 1, wherein the shift conversion comprises a low-temperature shift conversion stage, in which substantially exclusively a low-temperature water-gas shift reaction takes place.

6. The process according to claim 1, wherein the shift conversion comprises a high-temperature shift conversion stage, in which substantially exclusively a high-temperature water-gas shift reaction takes place.

7. The process according to claim 1, in that the methanol reactor assembly comprises a condensation stage for separating methanol and for obtaining the residual gas stream.

8. The process according to claim 7, wherein the methanol reactor assembly comprises a first reactor stage and a second reactor stage for the synthesis of methanol, in that the synthesis gas stream is supplied to the first reactor stage, and in that a further residual gas stream with unreacted carbon oxides from the first reactor stage is supplied to the second reactor stage, in that the condensation stage is arranged between the first reactor stage and the second reactor stage in the process sequence, and in that the residual gas stream and the further residual gas stream is obtained from the condensation stage.

9. The process according to claim 7, wherein the further reactant stream is a further synthesis gas stream, comprising hydrogen and carbon oxides, obtained from the synthesis gas reactor assembly, wherein an oxygen-containing stream is supplied to the synthesis gas reactor assembly, and in that synthesis gas for the synthesis gas stream, is obtained in a reactor of the synthesis gas reactor assembly by catalytic partial oxidation by means of the oxygen-containing stream.

10. The process according to claim 1, wherein the synthesis gas reactor assembly comprises a multi-stage waste heat utilisation, arranged downstream of the reactor in the process sequence, for recovering the heat from the recovery of the synthesis gas, and in that the synthesis gas stream and the further synthesis gas stream are obtained in each case after different stages of the waste heat utilisation.

11. The process according to claim 1, wherein the nitrogen stream is obtained from an air separation for obtaining molecular oxygen from the ambient air, in that the oxygen-containing stream is an oxygen stream obtained from the air separation.

12. The process according to claim 1, wherein a purge gas comprising carbon dioxide is obtained from the hydrogen recovery, in that substantially all carbon dioxide of the converted stream is removed in the hydrogen recovery so that the first hydrogen-containing stream and/or the second hydrogen-containing stream is substantially free of carbon dioxide.

13. The process according to claim 12, wherein the hydrogen recovery comprises a carbon dioxide scrubbing for at least partially washing the carbon dioxide out of the converted stream by means of a washing agent, in that the purge gas is at least partially obtained from the carbon dioxide wash.

14. The process according to claim 1, wherein the hydrogen recovery has a pressure swing adsorption plant, for recovering at least one of the first hydrogen-containing stream and the second hydrogen-containing stream, wherein the first hydrogen-containing stream comprises substantially hydrogen and is substantially free of carbon oxides.

* * * * *